(12) United States Patent
Hull

(10) Patent No.: US 6,845,671 B2
(45) Date of Patent: Jan. 25, 2005

(54) INVERSE METHOD TO ESTIMATE THE PROPERTIES OF A FLEXURAL BEAM AND THE CORRESPONDING BOUNDARY PARAMETERS

(75) Inventor: Andrew J Hull, Newport, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 33 days.

(21) Appl. No.: 10/263,294

(22) Filed: Sep. 27, 2002

(65) Prior Publication Data

US 2004/0065152 A1 Apr. 8, 2004

(51) Int. Cl.$^7$ .......................... G01N 3/00; G01H 13/00
(52) U.S. Cl. ............................ 73/574; 73/581; 73/789
(58) Field of Search .................... 73/574–575, 579, 73/581–583, 594, 786–789, 801, 587; 367/13

(56) References Cited

U.S. PATENT DOCUMENTS

| 5,519,637 | A | * | 5/1996 | Mathur | 700/280 |
| 5,526,694 | A | * | 6/1996 | McEachern et al. | 73/587 |
| 5,625,146 | A | * | 4/1997 | Hull | 73/574 |
| 5,808,965 | A | * | 9/1998 | Hull | 367/13 |
| 6,116,389 | A | * | 9/2000 | Allaei | 188/378 |
| 6,609,428 | B2 | * | 8/2003 | Hull | 73/789 |

* cited by examiner

Primary Examiner—Helen Kwok
(74) Attorney, Agent, or Firm—James M. Kasischke; Michael F. Oglo; Jean-Paul A. Nasser

(57) ABSTRACT

A system and method is used for estimating the properties of a flexural beam. The beam is shaken transverse to its longitudinal axis. Seven frequency domain transfer functions of displacement are measured at spaced apart locations along the beam. The seven transfer functions are combined to yield closed form values of the flexural wavenumber in propagation coefficients at any test frequency.

12 Claims, 12 Drawing Sheets

INVERSE METHOD TO ESTIMATE THE PROPERTIES OF A FLEXURAL BEAM AND THE CORRESPONDING BOUNDARY PARAMETERS

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

This invention relates to the field of structural properties, and in particular to the determination of the complex flexural wavenumber, corresponding wave propagation coefficients, and boundary condition parameters of a beam subjected to transverse motion.

(2) Description of the Prior Art

By way of example of the state of the art, reference is made to the following papers, which are incorporated herein by reference. Not all of these references may be deemed to be relevant prior art.

D. M. Norris, Jr., and W. C. Young, "Complex Modulus Measurements by Longitudinal Vibration Testing," Experimental Mechanics, Volume 10, 1970, pp. 93–96.

W. M. Madigosky and G. F. Lee, "Improved Resonance Technique for Materials Characterization," Journal of the Acoustical Society of America, Volume 73, Number 4, 1983, pp. 1374–1377.

S. L. Garrett, "Resonant Acoustic Determination of Elastic Moduli," Journal of the Acoustical Society of America, Volume 88, Number 1, 1990, pp. 210–220.

I. Jimeno-Fernandez, H. Uberall, W. M. Madigosky, and R. B. Fiorito, "Resonance Decomposition for the Vibratory Response of a Viscoelastic Rod," Journal of the Acoustical Society of America, Volume 91, Number 4, Part 1, April 1992, pp. 2030–2033.

G. F. Lee and B. Hartmann, "Material Characterizing System," U.S. Pat. No. 5,363,701, Nov. 15, 1994.

G. W. Rhodes, A. Migliori, and R. D. Dixon, "Method for Resonant Measurement," U.S. Pat. No. 5,495,763, Mar. 5, 1996.

R. F. Gibson and E. O. Ayorinde, "Method and Apparatus for Non-Destructive Measurement of Elastic Properties of Structural Materials," U.S. Pat. No. 5,533,399, Jul. 9, 1996.

B. J. Dobson, "A Straight-Line Technique for Extracting Modal Properties From Frequency Response Data," Mechanical Systems and Signal Processing, Volume 1, 1987, pp. 29–40.

C. Minas and D. J. Inman, "Matching Finite Element Models to Modal Data," Journal of Vibration and Acoustics, Volume 112, Number 1, 1990, pp. 84–92, T. Pritz, "Transfer Function Method for Investigating the Complex Modulus of Acoustic Materials: Rod-Like Specimen," Journal of Sound and Vibration, Volume 81, 1982, pp. 359–376.

W. M. Madigosky and G. F. Lee, "Instrument for Measuring Dynamic Viscoelastic Properties," U.S. Pat. No. 4,352,292, Oct. 5, 1982.

W. M. Madigosky and G. F. Lee, "Method for Measuring Material Characteristics," U.S. Pat. No. 4,418,573, Dec. 6, 1983.

W. Madigosky, "In Situ Dynamic Material Property Measurement System," U.S. Pat. No. 5,365,457, Nov. 15, 1994.

J. G. McDaniel, P. Dupont, and L. Salvino, "A Wave Approach to Estimating Frequency-Dependent Damping Under Transient Loading" Journal of Sound and Vibration, Volume 231(2), 2000, pp. 433–449.

J. Linjama and T. Lahti, "Measurement of Bending wave reflection and Impedance in a Beam by the Structural Intensity Technique" Journal of Sound and Vibration, Volume 161(2), 1993, pp. 317–331.

L. Koss and D. Karczub, "Euler Beam Bending Wave Solution Predictions of dynamic Strain Using Frequency Response Functions " Journal of Sound and Vibration, Volume 184(2), 1995, pp. 229–244.

Measuring the flexural properties of beams is important because these parameters significantly contribute to the static and dynamic response of structures. In the past, resonant techniques have been used to identify and measure longitudinal properties. These methods are based on comparing the measured eigenvalues of a structure to predicted eigenvalues from a model of the same structure. The model of the structure must have well-defined (typically closed form) eigenvalues for this method to work. Additionally, resonant techniques only allow measurements at natural frequencies.

Comparison of analytical models to measured frequency response functions is another method used to estimate stiffness and loss parameters of a structure. When the analytical model agrees with one or more frequency response functions, the parameters used to calculate the analytical model are considered accurate. If the analytical model is formulated using a numerical method, a comparison of the model to the data can be difficult due to the dispersion properties of the materials.

Another method to measure stiffness and loss is to deform the material and measure the resistance to the indentation. This method can physically damage the specimen if the deformation causes the sample to enter the plastic region of deformation.

SUMMARY OF THE INVENTION

Accordingly, one objective of the present invention is to measure flexural wavenumbers.

Another objective of the present invention is to measure flexural wave propagation coefficients.

A further objective of the present invention is to measure Young's modulus when the beam is undergoing transverse motion.

Yet another objective of the present invention is to measure the boundary stiffness and dampening values when the beam is vibrated transversely.

The foregoing objects are attained by the method and system of the present invention. The present invention features a method of determining structural properties of a flexural beam mounted to a base. The method comprises securing a plurality of accelerometers spaced approximately equidistant from each other along a length of a beam. One accelerometer can be secured to the base. An input is provided to the beam. Seven frequency domain transfer functions of displacement are measured from the accelerometers secured to the beam. The flexural wavenumber is estimated from the seven frequency domain transfer functions.

The seven frequency domain transfer functions of displacement include the following equations:

$$T_{-3} = \frac{U_{-3}(-3\alpha, \omega)}{V_0(\omega)} =$$

$$A\cos(3\alpha\delta) - B\sin(3\alpha\delta) + C\cosh(3\alpha\delta) - D\sinh(3\alpha\delta),$$

-continued $$T_{-2} = \frac{U_{-2}(-2\alpha, \omega)}{V_0(\omega)} =$$
$$A\cos(2\alpha\delta) - B\sin(2\alpha\delta) + C\cosh(2\alpha\delta) - D\sinh(2\alpha\delta),$$

$$T_{-1} = \frac{U_{-1}(-\alpha, \omega)}{V_0(\omega)} = A\cos(\alpha\delta) - B\sin(\alpha\delta) +$$
$$C\cosh(\alpha\delta) - D\sinh(\alpha\delta),$$

$$T_0 = \frac{U_0(0, \omega)}{V_0(\omega)} = A + C,$$

$$T_1 = \frac{U_1(\delta, \omega)}{V_0(\omega)} = A\cos(\alpha\delta) + B\sin(\alpha\delta) + C\cosh(\alpha\delta) + D\sinh(\alpha\delta),$$

$$T_2 = \frac{U_2(2\delta, \omega)}{V_0(\omega)} =$$
$$A\cos(2\alpha\delta) - B\sin(2\alpha\delta) + C\cosh(2\alpha\delta) + D\sinh(2\alpha\delta),$$

and $$T_3 = \frac{U_3(3\delta, \omega)}{V_0(\omega)} =$$
$$A\cos(3\alpha\delta) + B\sin(3\alpha\delta) + C\cosh(3\alpha\delta) + D\sinh(3\alpha\delta),$$

and

The flexural wavenumber is determined using the following equations:

$$\text{Re}(\alpha) = \begin{cases} \frac{1}{2\delta}\text{Arc }\cos(s) + \frac{n\pi}{2\delta} & n \text{ even} \\ \frac{1}{2\delta}\text{Arc }\cos(-s) + \frac{n\pi}{2\delta} & n \text{ odd} \end{cases} \text{ where}$$

$$s = [\text{Re}(\phi)]^2 + [\text{Im}(\phi)]^2 -$$
$$\sqrt{\{[\text{Re}(\phi)]^2 + [\text{Im}(\phi)]^2\}^2 - \{2[\text{Re}(\phi)]^2 + 2[\text{Im}(\phi)]^2 - 1\}}$$

and said imaginary part comprises:

$$\text{Im}(\alpha) = \frac{1}{\delta}\log_e\left\{\frac{\text{Re}(\phi)}{\cos[\text{Re}(\alpha)\delta]} - \frac{\text{Im}(\phi)}{\sin[\text{Re}(\alpha)\delta]}\right\}.$$

Using the flexural wavenumber and various equations disclosed within the present invention, the complex valued modulus of elasticity can be determined at each frequency, as well as the wave property coefficient, and the boundary parameters.

Thus, this invention has the advantages that all measurements can be calculated at every frequency that a transfer function measurement is made. They do not depend on system resonance's or curve fitting to transfer functions. The calculation from transfer function measurement to calculation of all system parameters is exact, i.e., no errors are introduced during this process. Furthermore, the measurements can be calculated without adverse consequences to the tested beam.

BRIEF DESCRIPTION OF THE DRAWINGS

These and other features and advantages of the present invention will be better understood in view of the following description of the invention taken together with the drawings wherein.

DESCRIPTION OF THE PREFERRED EMBODIMENT

The method and system, according to the present invention, is used to develop and measure complex flexural wavenumbers and the corresponding wave propagation coefficients of a beam undergoing transverse motion. An inverse method has been developed using seven transfer function measurements. These seven transfer function measurements are combined to yield closed form values of flexural wavenumber and wave propagation coefficients at any given test frequency. Finally, Young's modulus, spring stiffnesses, dashpot damping values, and boundary condition parameters, among other parameters, are calculated from the flexural wavenumber and wave propagation coefficients.

Figure 1:
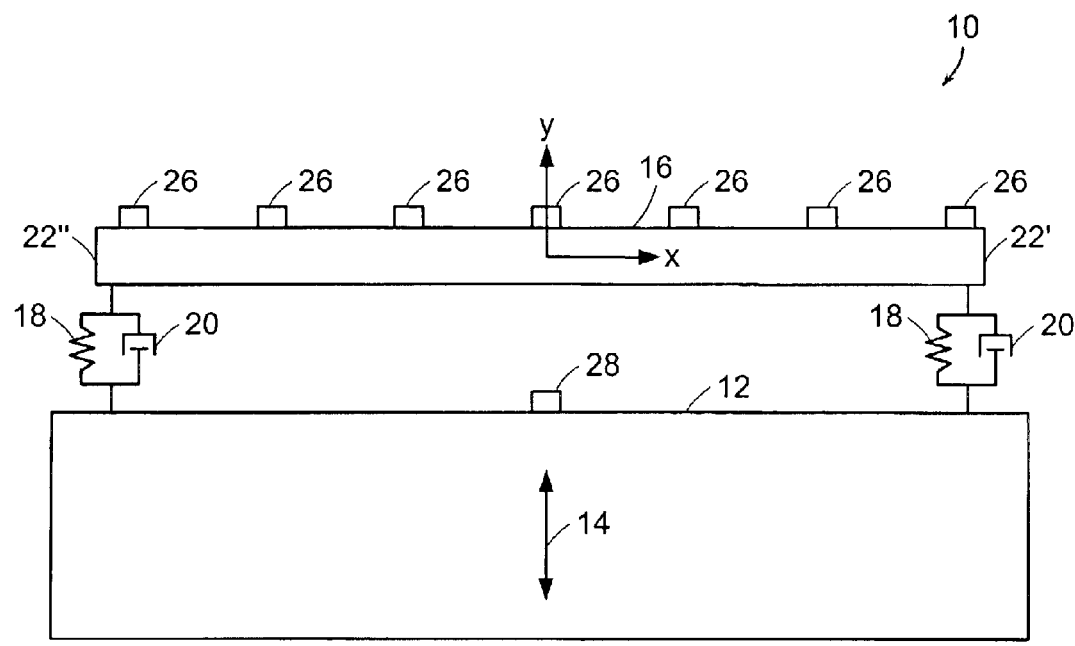
FIG. 1 is a schematic block diagram of a conventional testing system including two springs and two dashpots attached to a shaker table.
Figure 2:
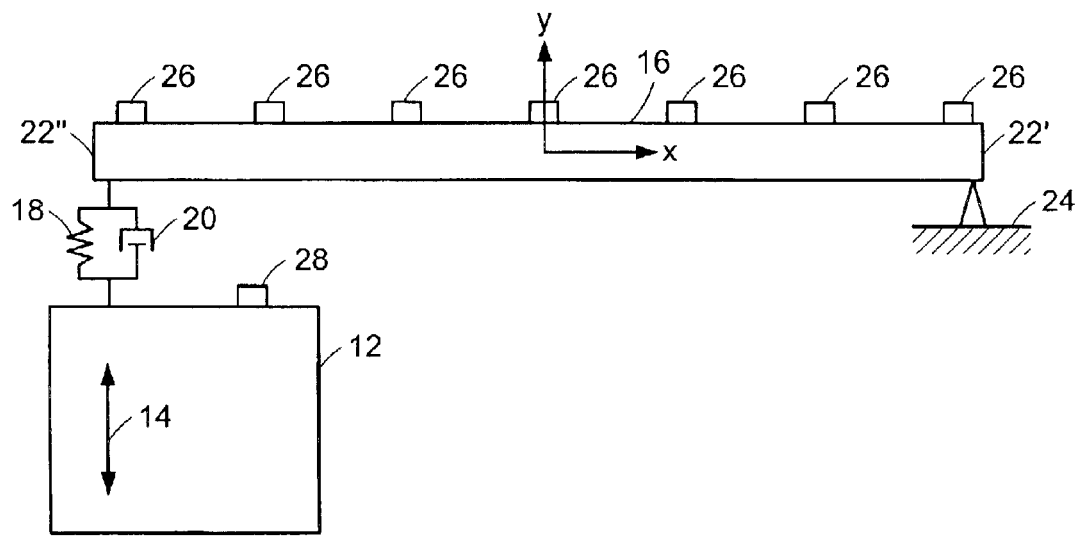
FIG. 2 is a schematic block diagram of a conventional testing system including one spring and one dashpot attached to a shaker table.
Figure 3:
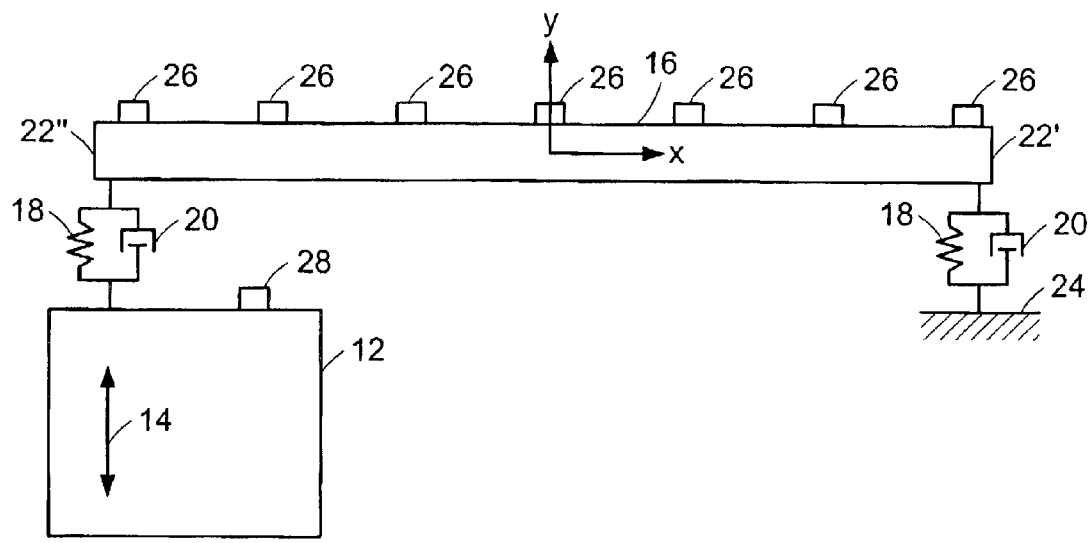
FIG. 3 is a schematic block diagram of a conventional testing system including two springs and two dashpots, one of which is attached to a shaker table.
Figure 4:
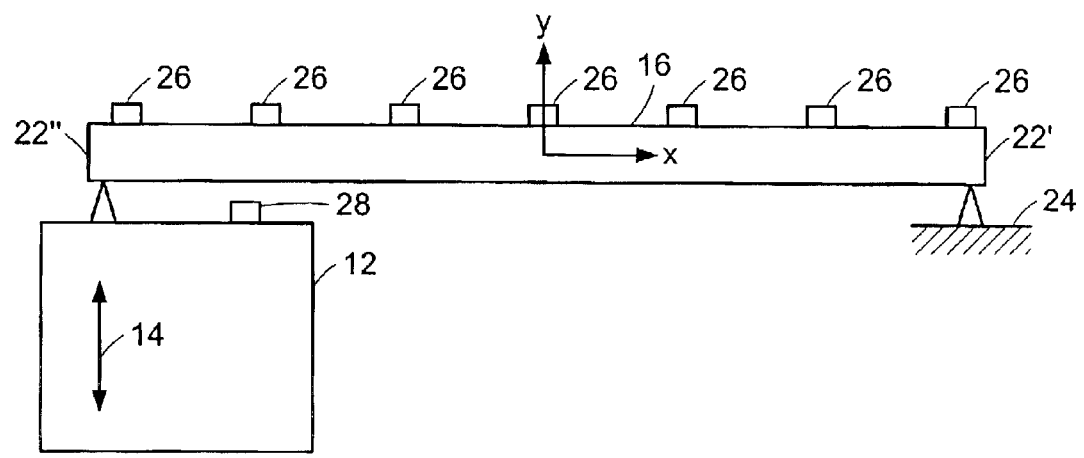
FIG. 4 is a schematic block diagram of a conventional testing system wherein the beam is attached directly to a shaker table.

According to an exemplary test configuration 10, FIG. 1, a shaker table 12 initiates transverse motion 14 into a beam 16. The beam 16 is connected to the shaker table 12 with a spring 18 and dashpot 20 at each end 22. FIG. 1 represents a double translational spring and damper input configuration. Other test configurations are also possible, including the shaker table 12 inputting energy into only one end 22 of the beam 16 with the other end terminated to ground 24 directly, as shown in FIG. 2, or terminated to ground 24 with a spring 18 and dashpot 20, as shown in FIG. 3, or terminated to ground 24 and the shaker 12 directly, as shown in FIG. 4. FIG. 2 represents a single translational spring and damper input configuration with the other end pinned. FIG. 3 represents a single translational spring and damper input configuration with the other end having a translational spring and damper. FIG. 4 represents a single pin input configuration with the other end pinned. These approaches are intended for use when a beam 16 is to undergo motion in the transverse direction 14. This system typically arises in cars, ships, aircraft, bridges, buildings and other common structures.

In any of the embodiments shown in FIGS. 1–4 sensors 26 such as accelerators are positioned equally along beam 22. As discussed above, a minimum of seven such sensors 22 are required. Optionally, a reference sensor 28 can be joined to shaker table 12 to read the input motion 14. The input motion 14 can also be read directly from the shaker table 12 controls.

For simplicity, the present invention will be described as it relates to the derivation of the linear equations of motion of the system with a spring 18 and dashpot 20 boundary condition at each end 22, but this is for exemplary purposes only, and is not intended to be a limitation.

The system model of the beam is the Bernoulli-Euler beam equation written as $$EI \frac{\partial^4 u(x,t)}{\partial x^4} + \rho A_b \frac{\partial^2 u(x,t)}{\partial t^2} = 0, \quad (1)$$

where x is the distance along the length of the beam in meters, t is time in seconds, u is the displacement of the beam in the (transverse) y direction in meters, E is the unknown frequency-dependent, complex Young's modulus (N/m$^2$), I is the moment of inertia (m$^4$), $\rho$ is the density (kg/m$^3$), and $A_b$ is the cross-sectional area of the beam (m$^2$). Implicit in equation (1) is the assumption that plane sections remain planar during bending (or transverse motion). Additionally, Young's modulus, the moment of inertia, the density, and the cross sectional area are constant across the entire length of the beam. The displacement is modeled as a steady state response and is expressed as $$u(x,t)=U(x,\omega)\exp(i\omega t), \quad (2)$$

where $\omega$ is the frequency of excitation (rad/s), $U(x,\omega)$ is the temporal Fourier transform of the transverse displacement, and i is the square root of $-1$. The temporal solution to equation (1), derived using equation (2) and written in terms of trigonometric functions, is $$U(x,\omega)=A(\omega)\cos[\alpha(\omega)x]+B(\omega)\sin[\alpha(\omega)x]+C(\omega)\cosh[\alpha(\omega)x]+D(\omega)\sinh[\alpha(\omega)x]' \quad (3)$$

where $A(\omega)$, $B(\omega)$, $C(\omega)$, and $D(\omega)$ are wave propagation coefficients and $\alpha(\omega)$ is the flexural wavenumber given by $$\alpha(\omega) = \left[\frac{\omega^2}{(EI/\rho A_b)}\right]^{1/4}. \quad (4)$$

For brevity, the $\omega$ dependence is omitted from the wave propagation coefficients and the flexural wavenumber during the remainder of the disclosure and $\alpha(\omega)$ is references as $\alpha$. Note that equations (3) and (4) are independent of boundary conditions, and the inverse model developed in the next section does not need boundary condition specifications. Boundary conditions are chosen, however, to show that the boundary parameters can be estimated and to run a realistic simulation.

One of the most typical test configurations is the beam mounted to shock mounts on each end that are attached to a shaker table that generates a vibrational input, as shown in FIG. 1. Using the middle of the beam as the coordinate system origin, these boundary conditions are modeled as $$\frac{\partial^2 u(-L/2,t)}{\partial x^2} = 0, \quad (5)$$

$$-EI\frac{\partial^3 u(-L/2,t)}{\partial x^3} = k_1[u(-L/2,t)-v(t)] + c_1\left[\frac{\partial u(-L/2,t)}{\partial t} - \frac{\partial v(t)}{\partial t}\right], \quad (6)$$

$$\frac{\partial^2 u(L/2,t)}{\partial x^2} = 0, \quad (7)$$

$$-EI\frac{\partial^3 u(L/2,t)}{\partial x^3} = k_2[u(L/2,t)-v(t)] + c_2\left[\frac{\partial u(L/2,t)}{\partial t} - \frac{\partial v(t)}{\partial t}\right], \quad (8)$$

where $$v(t)=V_0(\omega)\exp(i\omega t), \quad (9)$$

which is the input into the system from the shaker table.

Inserting equation (3) into equation (5), (6), (7), (8), and (9) yields the solution to the wave propagation coefficients. Inserting these back into equation (3) is the displacement of the system, and is sometimes called the forward solution. The wave coefficient A is $$A = \frac{A_T}{A_B}, \quad (10)$$

where $$A_T = [(k_1+i\omega c_1)-(k_2+i\omega c_2)] \quad (11)$$
$$(EI\alpha^3)\cos\left(\alpha\frac{L}{2}\right)\cosh\left(\alpha\frac{L}{2}\right)\sinh\left(\alpha\frac{L}{2}\right) -$$
$$[(k_1+i\omega c_1)-(k_2+i\omega c_2)](EI\alpha^3)\sin\left(\alpha\frac{L}{2}\right)\cosh^2\left(\alpha\frac{L}{2}\right) -$$
$$4(k_1+i\omega c_1)(k_2+i\omega c_2)\sin\left(\alpha\frac{L}{2}\right)$$
$$\cosh\left(\alpha\frac{L}{2}\right)\sinh\left(\alpha\frac{L}{2}\right), \text{ and}$$

$$A_B = 2(EI\alpha^3)^2\sin^2\left(\alpha\frac{L}{2}\right)\cosh\left(\alpha\frac{L}{2}\right) - \quad (12)$$
$$2[(k_1+i\omega c_1)-(k_2+i\omega c_2)](EI\alpha^3)\sin^2\left(\alpha\frac{L}{2}\right)\cosh\left(\alpha\frac{L}{2}\right)$$
$$\sinh\left(\alpha\frac{L}{2}\right) - 2(EI\alpha^3)^2\cos^2\left(\alpha\frac{L}{2}\right)\sinh^2\left(\alpha\frac{L}{2}\right) -$$
$$2[(k_1+i\omega c_1)-(k_2+i\omega c_2)](EI\alpha^3)\cos\left(\alpha\frac{L}{2}\right)$$
$$\sin\left(\alpha\frac{L}{2}\right)\sinh^2\left(\alpha\frac{L}{2}\right) + 2[(k_1+i\omega c_1)-(k_2 i\omega c_2)]$$
$$(EI\alpha^3)\cos^2\left(\alpha\frac{L}{2}\right)\cosh\left(\alpha\frac{L}{2}\right)\sinh\left(\alpha\frac{L}{2}\right) -$$
$$2[(k_1+i\omega c_1)-(k_2+i\omega c_2)](EI\alpha^3)\cos\left(\alpha\frac{L}{2}\right)$$
$$\sin\left(\alpha\frac{L}{2}\right)\cosh^2\left(\alpha\frac{L}{2}\right) - 8(k_1+i\omega c_1)(k_2+i\omega c_2)$$
$$\cos\left(\alpha\frac{L}{2}\right)\sin\left(\alpha\frac{L}{2}\right)\cosh\left(\alpha\frac{L}{2}\right)\sinh\left(\alpha\frac{L}{2}\right)$$

The wave coefficient B is $$B = \frac{B_T}{B_B}, \quad (13)$$

where $$B_T = -[(k_1+i\omega c_1)+(k_2 i\omega c_2)] \quad (14)$$
$$(EI\alpha^3)\sin\left(\alpha\frac{L}{2}\right)\cosh\left(\alpha\frac{L}{2}\right)\sinh\left(\alpha\frac{L}{2}\right) -$$
$$[(k_1+i\omega c_1)+(k_2+i\omega c_2)](EI\alpha^3)\cos\left(\alpha\frac{L}{2}\right)\sinh^2\left(\alpha\frac{L}{2}\right), \text{ and}$$

-continued $$B_B = 2(EI\alpha^3)^2\cos^2\left(\alpha\frac{L}{2}\right)\sinh^2\left(\alpha\frac{L}{2}\right) - \quad (15)$$

$$2[(k_1 + i\omega c_1) - (k_2 + i\omega c_2)](EI\alpha^3)\cos^2\left(\alpha\frac{L}{2}\right)\cosh\left(\alpha\frac{L}{2}\right)$$

$$\sinh\left(\alpha\frac{L}{2}\right) - 2(EI\alpha^3)^2\sin^2\left(\alpha\frac{L}{2}\right)\cosh^2\left(\alpha\frac{L}{2}\right) +$$

$$2[(k_1 + i\omega c_1) - (k_2 + i\omega c_2)](EI\alpha^3)\cos\left(\alpha\frac{L}{2}\right)\sin\left(\alpha\frac{L}{2}\right)$$

$$\cosh^2\left(\alpha\frac{L}{2}\right) + 2[(k_1 + i\omega c_1) - (k_2 + i\omega c_2)]$$

$$(EI\alpha^3)\sin^2\left(\alpha\frac{L}{2}\right)\cosh\left(\alpha\frac{L}{2}\right)\sinh\left(\alpha\frac{L}{2}\right) +$$

$$2[(k_1 + i\omega c_1) - (k_2 + i\omega c_2)](EI\alpha^3)\cos\left(\alpha\frac{L}{2}\right)$$

$$\sin\left(\alpha\frac{L}{2}\right)\sinh^2\left(\alpha\frac{L}{2}\right) + 8(k_1 + i\omega c_1)(k_2 + i\omega c_2)$$

$$\cos\left(\alpha\frac{L}{2}\right)\sin\left(\alpha\frac{L}{2}\right)\cosh\left(\alpha\frac{L}{2}\right)\sinh\left(\alpha\frac{L}{2}\right)$$

The wave coefficient C is $$C = \frac{C_T}{A_B}, \quad (16)$$

where $$C_T = [(k_1 + i\omega c_1) - (k_2 + i\omega c_2)](EI\alpha^3)\cos^2\left(\alpha\frac{L}{2}\right)\sinh\left(\alpha\frac{L}{2}\right) - \quad (17)$$

$$[(k_1 + i\omega c_1) - (k_2 + i\omega c_2)](EI\alpha^3)\cos\left(\alpha\frac{L}{2}\right)\sin\left(\alpha\frac{L}{2}\right)\cosh\left(\alpha\frac{L}{2}\right) -$$

$$4(k_1 + i\omega c_1)(k_2 + i\omega c_2)\cos\left(\alpha\frac{L}{2}\right)\sin\left(\alpha\frac{L}{2}\right)\sinh\left(\alpha\frac{L}{2}\right).$$

The wave coefficient D is $$D = \frac{D_T}{B_B}, \quad (18)$$

where $$D_T = -[(k_1 + i\omega c_1) + (k_2 + i\omega c_2)](EI\alpha^3)\sin^2\left(\alpha\frac{L}{2}\right)\cosh\left(\alpha\frac{L}{2}\right) - \quad (19)$$

$$[(k_1 + i\omega c_1) + (k_2 + i\omega c_2)](EI\alpha^3)\cos\left(\alpha\frac{L}{2}\right)\sin\left(\alpha\frac{L}{2}\right)\sinh\left(\alpha\frac{L}{2}\right).$$

These coefficients are used for the simulation below. If the beam model corresponds to FIGS. 2, 3, or 4, then the boundary conditions given in equations (5)–(8) change slightly as do the wave propagation coefficients.

Equation (3) has five unknowns and is nonlinear with respect to the unknown flexural wavenumber. It will be shown that using seven independent, equally spaced measurements, that the five unknowns can be estimated with closed form solutions. Furthermore, in the next section, it will be shown that the components that comprise the beams mounting system can also be estimated. Seven frequency domain transfer functions of displacement are now measured. These consist of the measurement at some location divided by a common measurement. Typically this would be an accelerometer at a measurement location and an accelerometer at the base of a shaker table. These seven measurements are set equal the theoretical expression given in equation (3) and are listed as $$T_{-3} = \quad (20)$$
$$\frac{U_{-3}(-3\delta, \omega)}{V_0(\omega)} = A\cos(3\alpha\delta) - B\sin(3\alpha\delta) + C\cosh(3\alpha\delta) - D\sinh(3\alpha\delta),$$

$$T_{-2} = \quad (21)$$
$$\frac{U_{-2}(-2\delta, \omega)}{V_0(\omega)} = A\cos(2\alpha\delta) - B\sin(2\alpha\delta) + C\cosh(2\alpha\delta) - D\sinh(2\alpha\delta),$$

$$T_{-1} = \frac{U_{-1}(-\delta, \omega)}{V_0(\omega)} = A\cos(\alpha\delta) - B\sin(\alpha\delta) + C\cosh(\alpha\delta) - D\sinh(\alpha\delta), \quad (22)$$

$$T_0 = \frac{U_0(0, \omega)}{V_0(\omega)} = A + C, \quad (23)$$

$$T_1 = \frac{U_1(\delta, \omega)}{V_0(\omega)} = A\cos(\alpha\delta) + B\sin(\alpha\delta) + C\cosh(\alpha\delta) + D\sinh(\alpha\delta), \quad (24)$$

$$T_2 = \frac{U_2(2\delta, \omega)}{V_0(\omega)} = A\cos(2\alpha\delta) + B\sin(2\alpha\delta) + C\cosh(2\alpha\delta) + D\sinh(2\alpha\delta), \quad (25)$$

and $$T_3 = \frac{U_3(3\delta, \omega)}{V_0(\omega)} = A\cos(3\alpha\delta) + B\sin(3\alpha\delta) + C\cosh(3\alpha\delta) + D\sinh(3\alpha\delta), \quad (26)$$

where δ is the sensor to sensor separation distance (m) and $V_0(\omega)$ is the reference measurement. Note that the units of the transfer functions given in equations (20)–(26) are dimensionless.

Equation (22) is now subtracted from equation (24), equation (21) is subtracted from equation (25), and equation (20) is subtracted from equation (26), yielding the following three equations:

$$B\sin(\alpha\delta) + D\sinh(\alpha\delta) = \frac{T_1 - T_{-1}}{2}, \quad (27)$$

$$B\sin(2\alpha\delta) + D\sinh(2\alpha\delta) = \frac{T_2 - T_{-2}}{2}, \text{ and} \quad (28)$$

$$B\sin(3\alpha\delta) + D\sinh(3\alpha\delta) = \frac{T_3 - T_{-3}}{2}. \quad (29)$$

Equations (27), (28), and (29) are now combined to give $$\cosh(\alpha\delta)\cos(\alpha\delta) - \left[\frac{T_2 - T_{-2}}{2(T_1 - T_{-1})}\right][\cosh(\alpha\delta) + \cos(\alpha\delta)] + \left[\frac{T_3 - T_{-3} + T_1 - T_{-1}}{4(T_1 - T_{-1})}\right] = 0. \quad (30)$$

Equation (22) is now added to equation (24) and equation (21) is added to equation (25), yielding the following two equations:

$$A\cos(\alpha\delta) + C\cosh(\alpha\delta) = \frac{T_1 + T_{-1}}{2}, \quad (31)$$

and $$A\cos(2\alpha\delta) + C\cosh(2\alpha\delta) = \frac{T_2 + T_{-2}}{2}. \quad (32)$$

Equations (23), (31), and (32) are now combined to yield the following equation:

$$\cosh(\alpha\delta)\cos(\alpha\delta) - \left[\frac{T_2 - T_{-2}}{2T_0}\right][\cosh(\alpha\delta) + \cos(\alpha\delta)] + \left[\frac{T_2 + T_{-2} + 2T_0}{4T_0}\right] = 0. \quad (33)$$

Equation (30) and (33) are now combined, and the result is a binomial expression with respect to the cosine function, and is written as $$a\cos^2(\alpha\delta) + b\cos(\alpha\delta) + c = 0, \quad (34)$$

where $$a = 4T_1^2 - 4T_{-1}^2 + 4T_{-2}T_0 - 4T_0 T_2, \quad (35)$$

$$b = 2T_{-2}T_{-1} - 2T_{-2}T_1 + 2T_{-1}T_0 - 2T_0 T_1 + 2T_{-1}T_2 - 2T_1 T_2 + 2T_0 T_3 - 2T_{-3}T_0, \quad (36)$$

and $$c = T_{-1}^2 - T_1^2 + T_2^2 - T_{-2}^2 + T_{-3}T_{-1} - T_{-1}T_3 + T_{-3}T_1 - T_1 T_3 + 2T_0 T_2 - 2T_{-2}T_0. \quad (37)$$

Equation (34) is now solved using $$\cos(\alpha\delta) = \frac{-b \pm \sqrt{b^2 - 4ac}}{2a} = \phi, \quad (38)$$

where $\phi$ is typically a complex number. Equation (38) is two solutions to equation (34). One, however, will have an absolute value less than one and that is the root that is further manipulated. The inversion of equation (38) allows the complex flexural wavenumber $\alpha$ to be solved as a function of $\phi$ at every frequency in which a measurement is made. The solution to the real part of $\alpha$ is $$\mathrm{Re}(\alpha) = \begin{cases} \dfrac{1}{2\delta}\mathrm{Arccos}(s) + \dfrac{n\pi}{2\delta} & n \text{ even} \\ \dfrac{1}{2\delta}\mathrm{Arccos}(-s) + \dfrac{n\pi}{2\delta} & n \text{ odd} \end{cases}, \quad (39)$$

where $$s = [\mathrm{Re}(\phi)]^2 + [\mathrm{Im}(\phi)]^2 - \sqrt{\{[\mathrm{Re}(\phi)]^2 + [\mathrm{Im}(\phi)]^2\}^2 - \{2[\mathrm{Re}(\phi)]^2 - 2[\mathrm{Im}(\phi)]^2 - 1\}}, \quad (40)$$

n is a non-negative integer and the capital A denotes the principal value of the inverse cosine function. The value of n is determined from the function s, which is a periodically varying cosine function with respect to frequency. At zero frequency, n is 0. Every time s cycles through $\pi$ radians (180 degrees), n is increased by 1. When the solution to the real part of $\alpha$ is found, the solution to the imaginary part of $\alpha$ is then written as $$\mathrm{Im}(\alpha) = \frac{1}{\delta}\log_e\left\{\frac{\mathrm{Re}(\phi)}{\cos[\mathrm{Re}(\alpha)\delta]} - \frac{\mathrm{Im}(\phi)}{\sin[\mathrm{Re}(\alpha)\delta]}\right\}. \quad (41)$$

Once the real and imaginary parts of wavenumber $\alpha$ are known, the complex valued modulus of elasticity can be determined at each frequency with $$E(\omega) = \mathrm{Re}[E(\omega)] + i\mathrm{Im}[E(\omega)] = \frac{\rho A_b \omega^2}{I[\mathrm{Re}(\alpha) + i\mathrm{Im}(\alpha)]^4}. \quad (42)$$

assuming that the density, area, and moment of inertia of the beam are known. Equations (20)–(42) produce an estimate Young's modulus at every frequency in which a measurement is conducted.

Additionally, combining equations (27) and (28) yields $$B = \frac{2(T_1 - T_{-1})\cosh(\alpha\delta) - (T_2 - T_{-2})}{4\sin(\alpha\delta)[\cosh(\alpha\delta) - \cos(\alpha\delta)]} \quad (43)$$

and $$D = \frac{(T_2 - T_{-2}) - 2(T_1 - T_{-1})\cos(\alpha\delta)}{4\sinh(\alpha\delta)[\cosh(\alpha\delta) - \cos(\alpha\delta)]}. \quad (44)$$

Combining equations (23) and (31) yields $$A = \frac{2T_0 \cosh(\alpha\delta) - (T_1 + T_{-1})}{2[\cosh(\alpha\delta) - \cos(\alpha\delta)]} \quad (45)$$

and $$C = \frac{(T_1 + T_{-1}) - 2T_0 \cos(\alpha\delta)}{2[\cosh(\alpha\delta) - \cos(\alpha\delta)]}. \quad (46)$$

Equations (43)–(46) are the estimates of the complex wave propagation coefficients. These are normally considered less important than the estimate of the flexural wavenumber. It will be shown, however, that these coefficients can be used to estimate the boundary condition parameters of the beam.

Inserting equations (2), (3), (4), and (9) into equation (6) and solving for the boundary parameters at $x = -L/2$ yields $$k_1 = \mathrm{Re}\left\{\frac{(EI\alpha^3)\left[A\sin\left(\alpha\frac{L}{2}\right) + B\cos\left(\alpha\frac{L}{2}\right) + C\sinh\left(\alpha\frac{L}{2}\right) - D\cosh\left(\alpha\frac{L}{2}\right)\right]}{\left[A\cos\left(\alpha\frac{L}{2}\right) - B\sin\left(\alpha\frac{L}{2}\right) + C\cosh\left(\alpha\frac{L}{2}\right) - D\sinh\left(\alpha\frac{L}{2}\right) - 1\right]}\right\} \quad (47)$$

and $$c_1 = \frac{1}{\omega}\mathrm{Im}\left\{\frac{(EI\alpha^3)\left[A\sin\left(\alpha\frac{L}{2}\right) + B\cos\left(\alpha\frac{L}{2}\right) + C\sinh\left(\alpha\frac{L}{2}\right) - D\cosh\left(\alpha\frac{L}{2}\right)\right]}{\left[A\cos\left(\alpha\frac{L}{2}\right) - B\sin\left(\alpha\frac{L}{2}\right) + C\cosh\left(\alpha\frac{L}{2}\right) - D\sinh\left(\alpha\frac{L}{2}\right) - 1\right]}\right\}. \quad (48)$$

Similarly, inserting equations (2), (3), (4), and (9) into equation (8) and solving for the boundary parameters at x=L/2 yields $$k_2 = \text{Re}\left\{\frac{(-EI\alpha^3)\left[A\sin\left(\alpha\frac{L}{2}\right) - B\cos\left(\alpha\frac{L}{2}\right) + C\sinh\left(\alpha\frac{L}{2}\right) + D\cosh\left(\alpha\frac{L}{2}\right)\right]}{\left[A\cos\left(\alpha\frac{L}{2}\right) + B\sin\left(\alpha\frac{L}{2}\right) + C\cosh\left(\alpha\frac{L}{2}\right) + D\sinh\left(\alpha\frac{L}{2}\right) - 1\right]}\right\} \quad (49)$$

and $$c_2 = \frac{1}{\omega}\text{Im}\left\{\frac{(-EI\alpha^3)\left[A\sin\left(\alpha\frac{L}{2}\right) - B\cos\left(\alpha\frac{L}{2}\right) + C\sinh\left(\alpha\frac{L}{2}\right) + D\cosh\left(\alpha\frac{L}{2}\right)\right]}{\left[A\cos\left(\alpha\frac{L}{2}\right) + B\sin\left(\alpha\frac{L}{2}\right) + C\cosh\left(\alpha\frac{L}{2}\right) + D\sinh\left(\alpha\frac{L}{2}\right) - 1\right]}\right\}. \quad (50)$$

Thus, once the flexural wavenumber and wave coefficients are estimated, the properties of the springs and dashpots at the boundaries can be calculated.

Figure 5A:
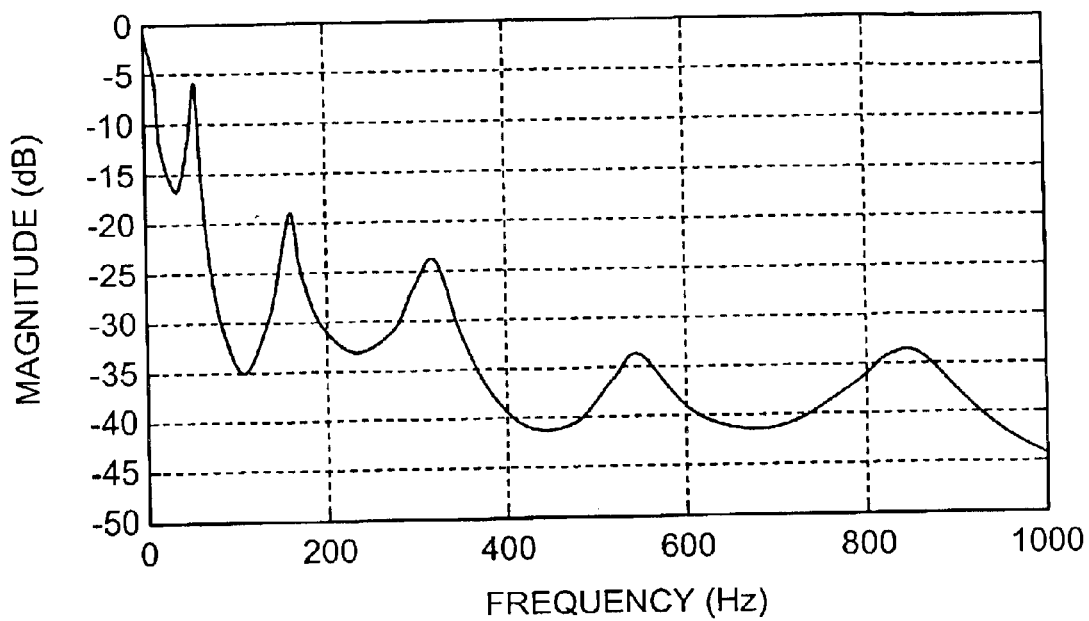
FIG. 5A is a graph of the magnitude of a typical transfer function of a beam.
Figure 5B:
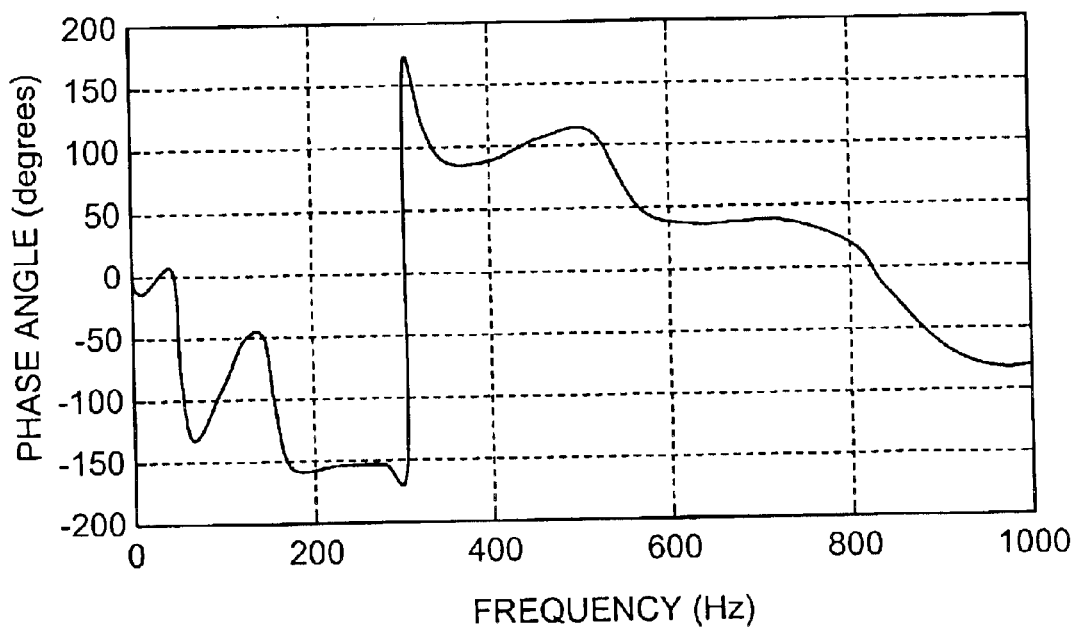
FIG. 5B is a graph of the phase angle of a typical transfer function of a beam.

Numerical simulations conducted to determine the effectiveness of this method use the following parameters to define a baseline problem: $\text{Re}(E)=(3\cdot10^{10}+10^7 f)$ N/m$^2$, $\text{Im}(E)=(3\cdot10^9+10^6 f)$ N/m$^2$, $\rho=5000$ kg/m$^3$, $A_b=0.02$ m$^2$, $I=6.67\times10^{-5}$ m$^4$, $L=3$ m, $\delta=0.5$ m, $k_1=50000$ N/m, $c_1=4000$ N·s/m, $k_2=60000$ N/m, and $c_2=5000$ N·s/m where f is frequency in Hz. FIGS. 5A and 5B represent a typical transfer function of the beam displacement measured at x=0 m, which is the middle of the beam, divided by base displacement. The top plot, FIG. 5A, is the magnitude versus frequency and the bottom plot, FIG. 5B, is the phase angle versus frequency. This figure was constructed by inserting the above parameters into equations (3), (4), (10), (11), (12), (13), (14), (15), (16), (17), (18), and (19) and calculating the solution (a forward model).

Figure 6:
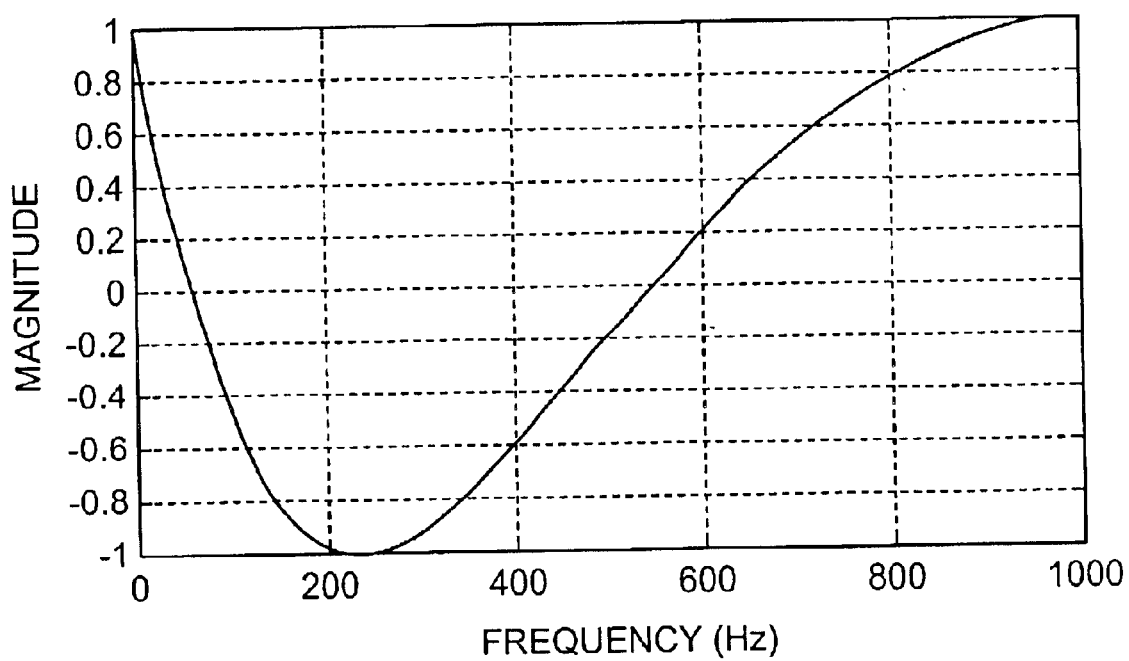
FIG. 6 is a graph of the function s versus frequency.
Figure 7A:
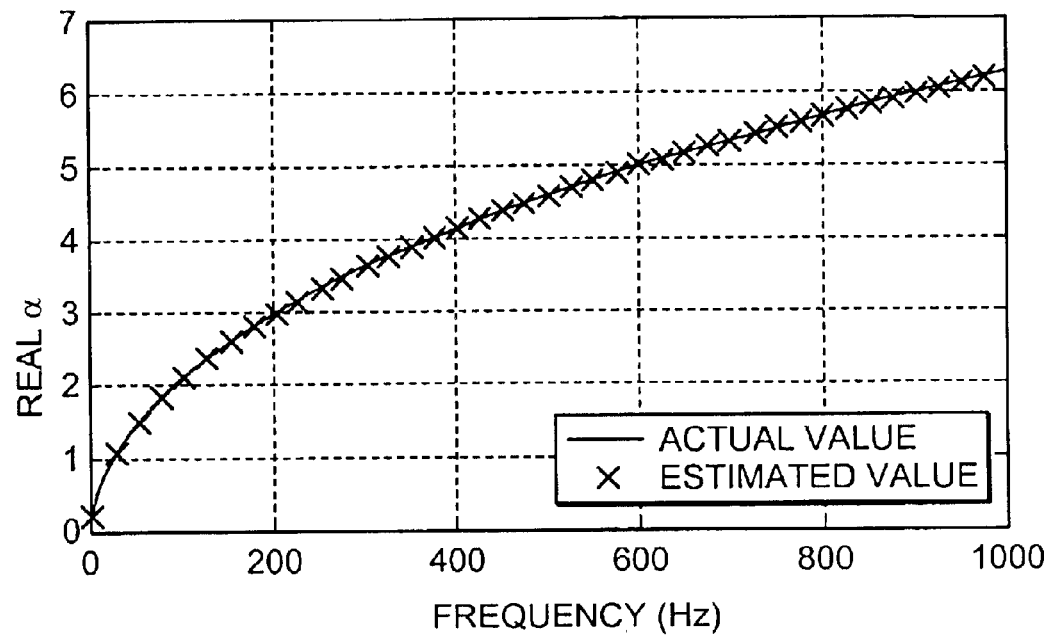
FIG. 7A is a graph of the real part of a flexural wavenumber versus frequency.
Figure 7B:
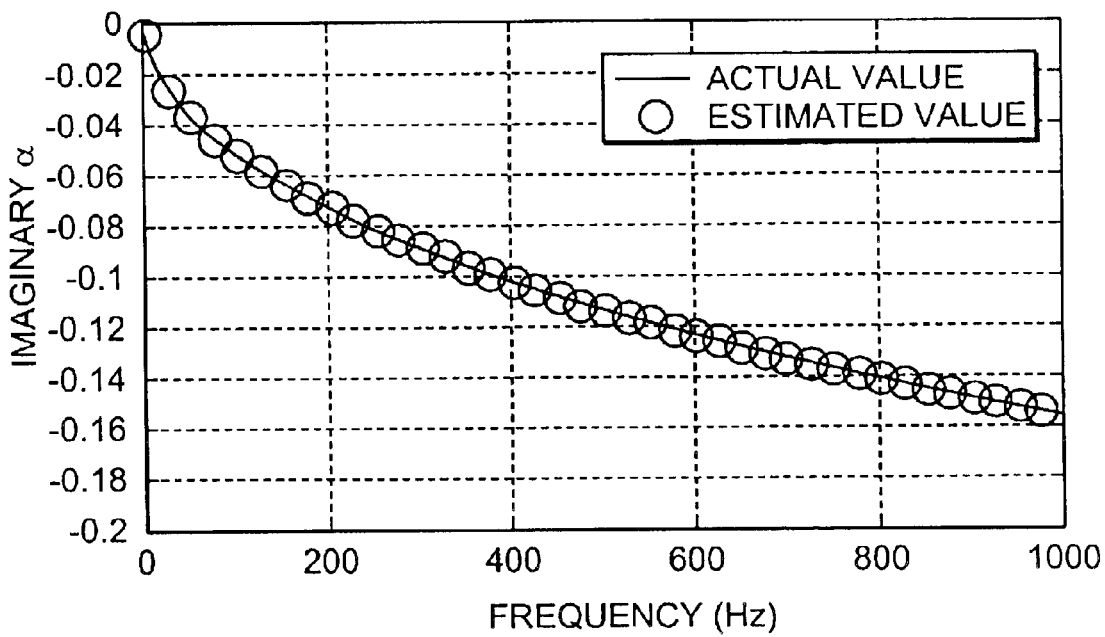
FIG. 7B is a graph of the imaginary part of a flexural wavenumber versus frequency.
Figure 8A:
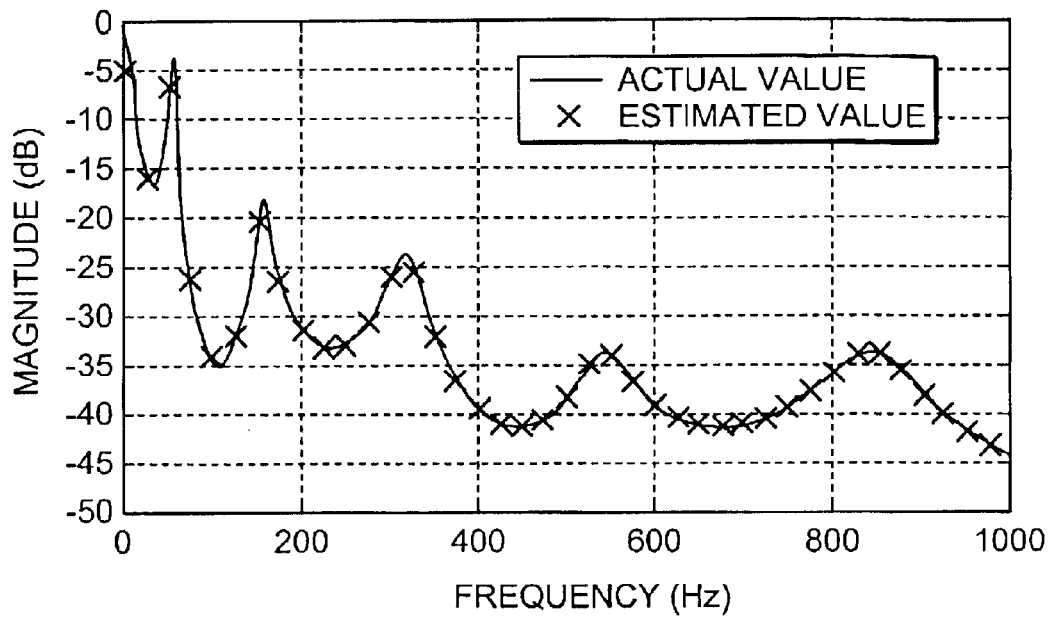
FIGS. 8–11 are graphs of the wave propagation coefficients versus frequency.
Figure 8B:
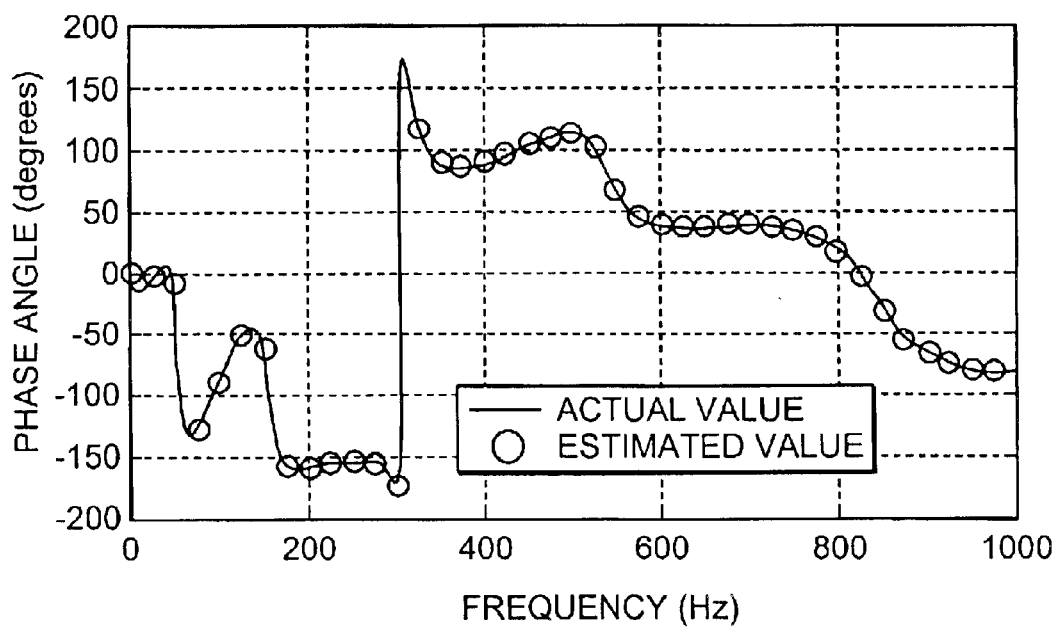
Figure 9A:
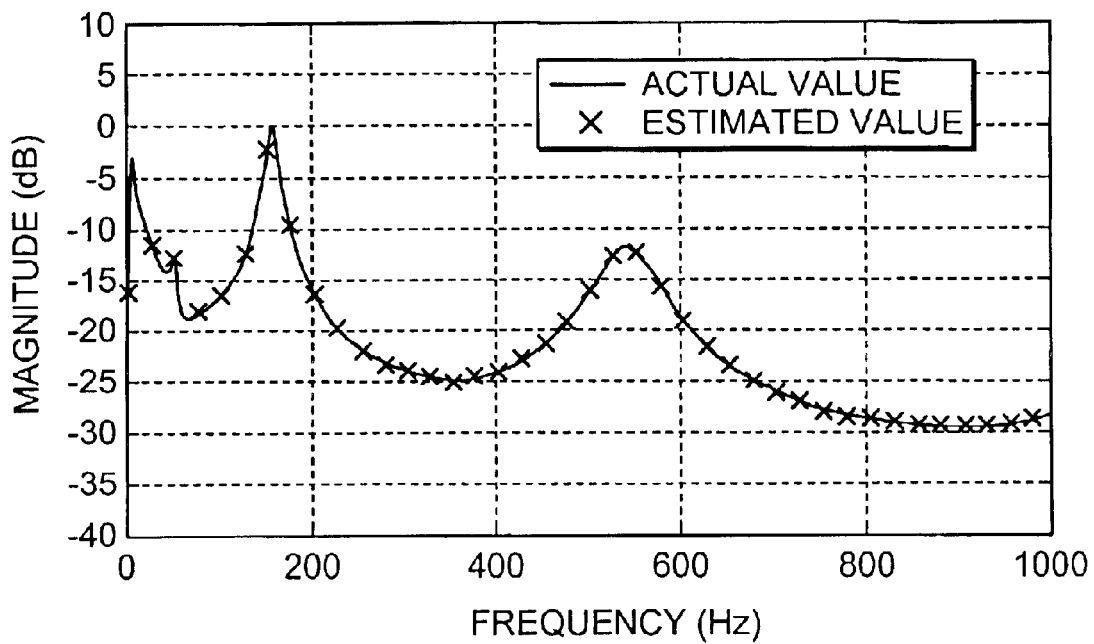
Figure 9B:
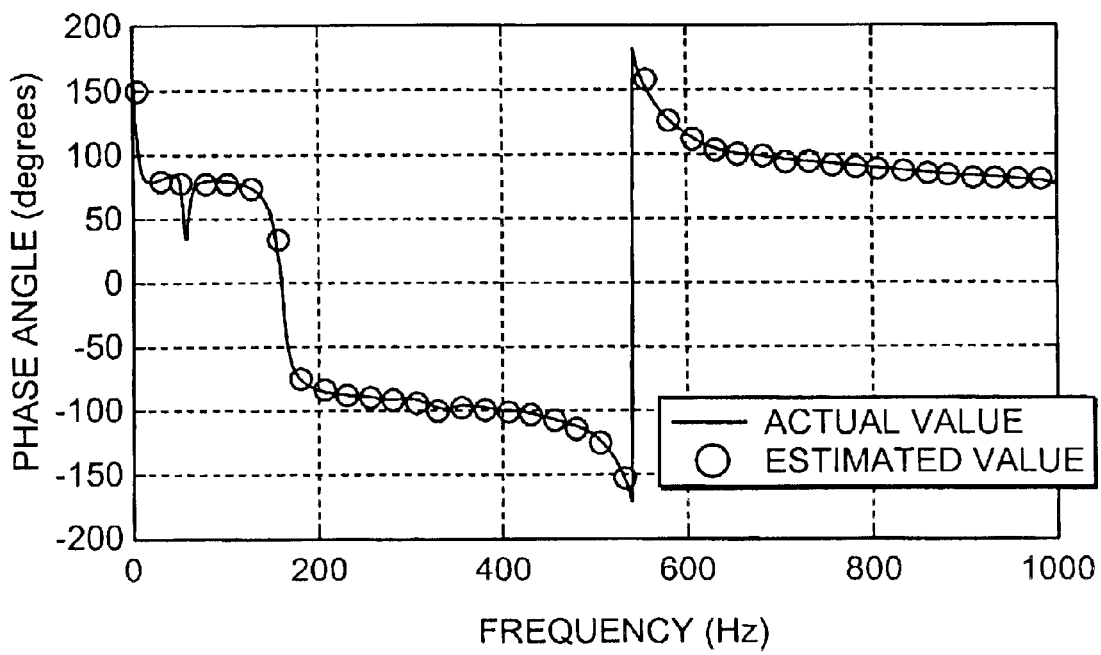
Figure 10A:
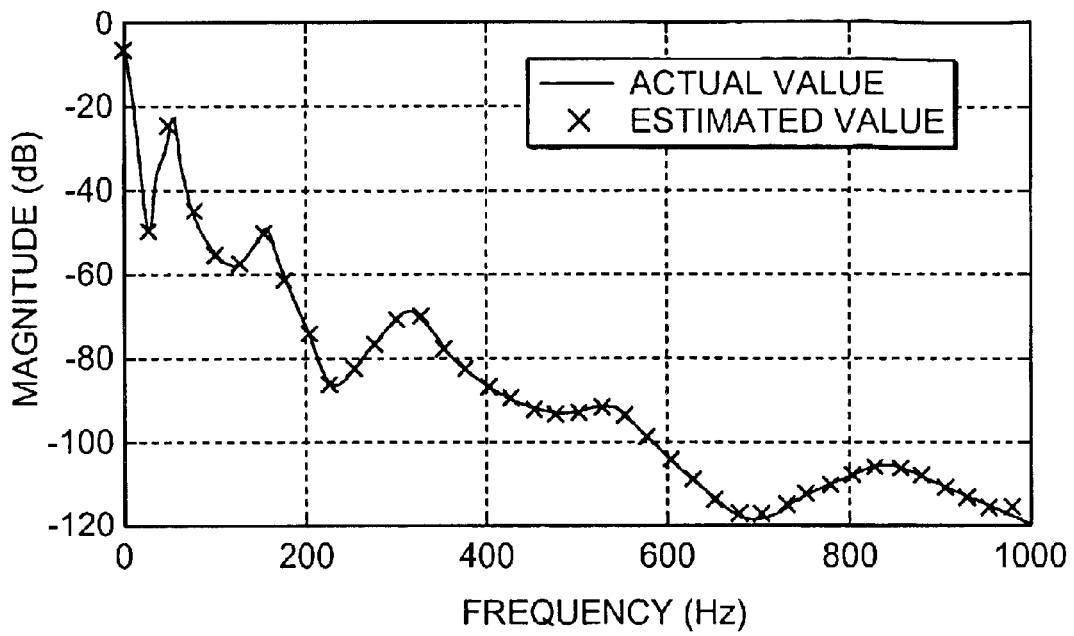
Figure 10B:
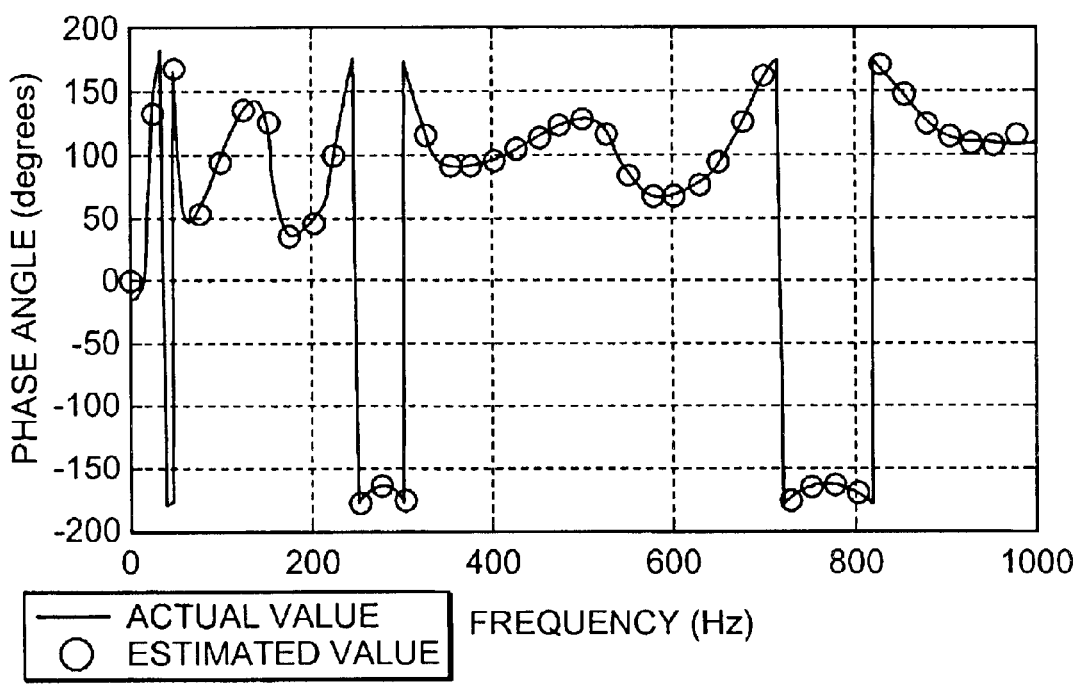
Figure 11A:
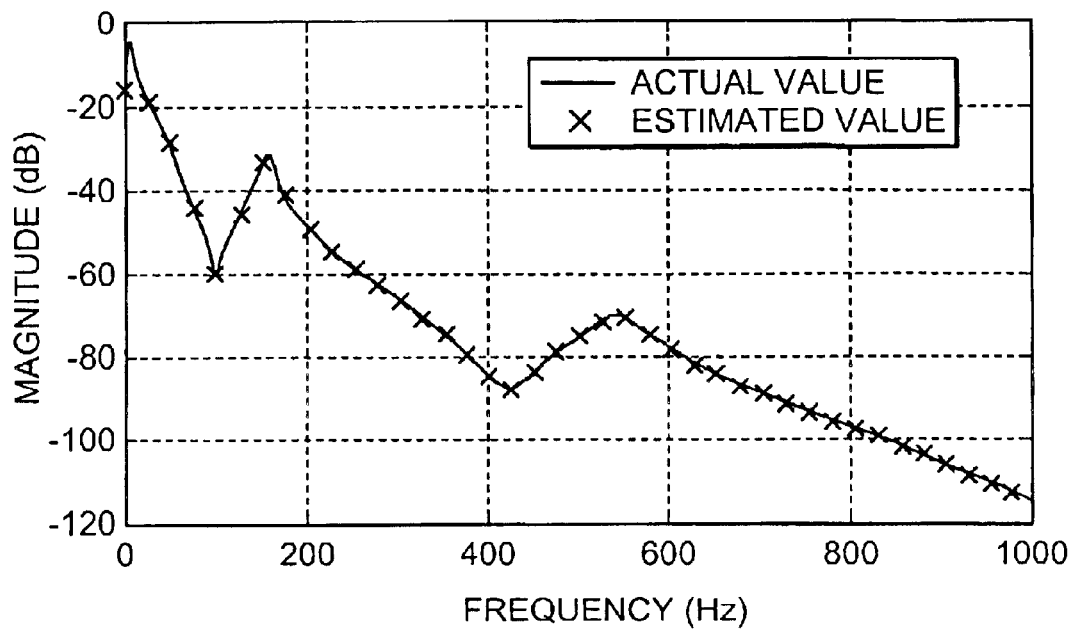
Figure 11B:
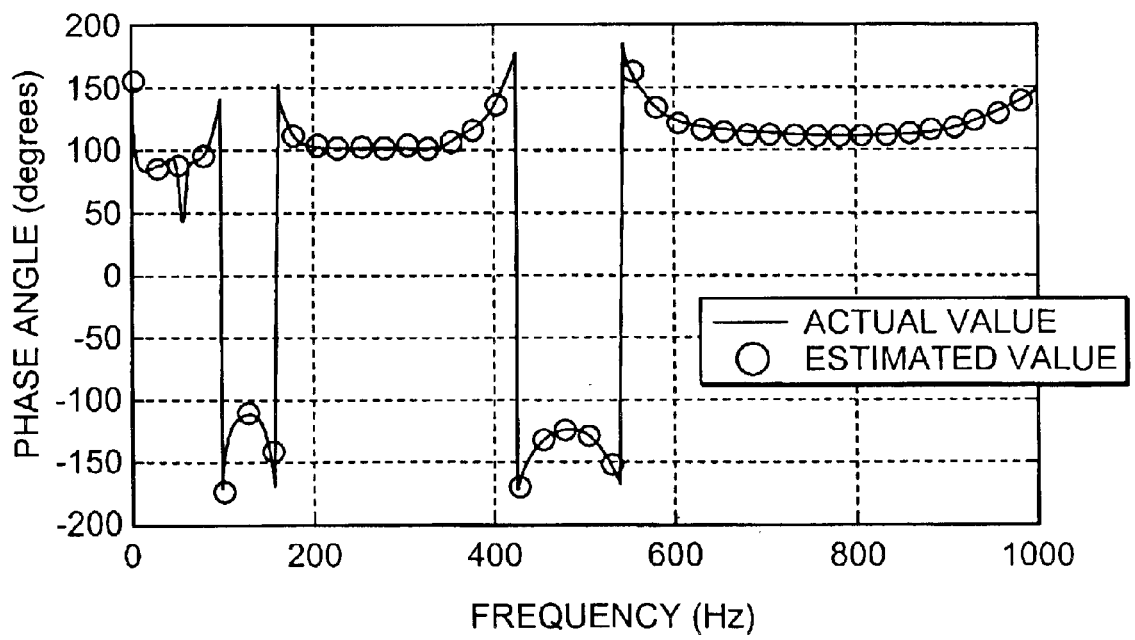
Figure 12:
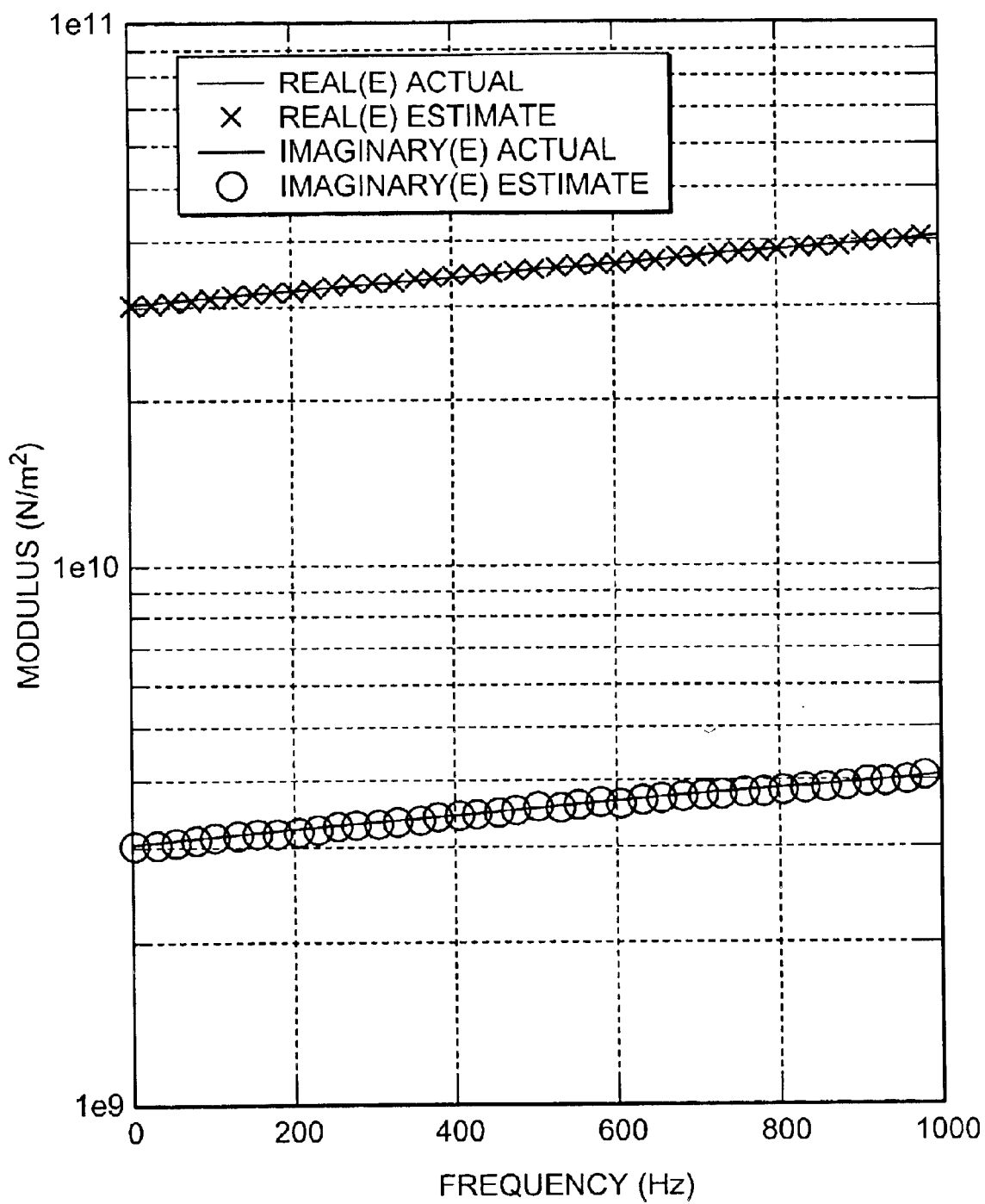
FIG. 12 is a graph of the real and imaginary parts of the Young's Modulus versus frequency.
Figure 13A:
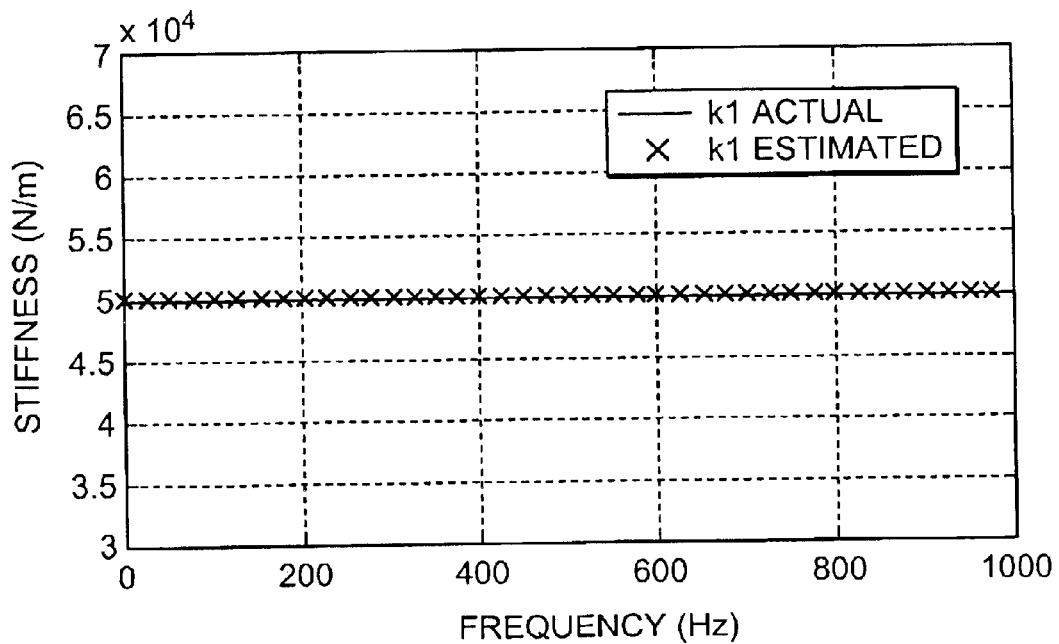
FIG. 13 is a graph of the boundary conditions of the system shown in FIG. 1 versus frequency.
Figure 13B:
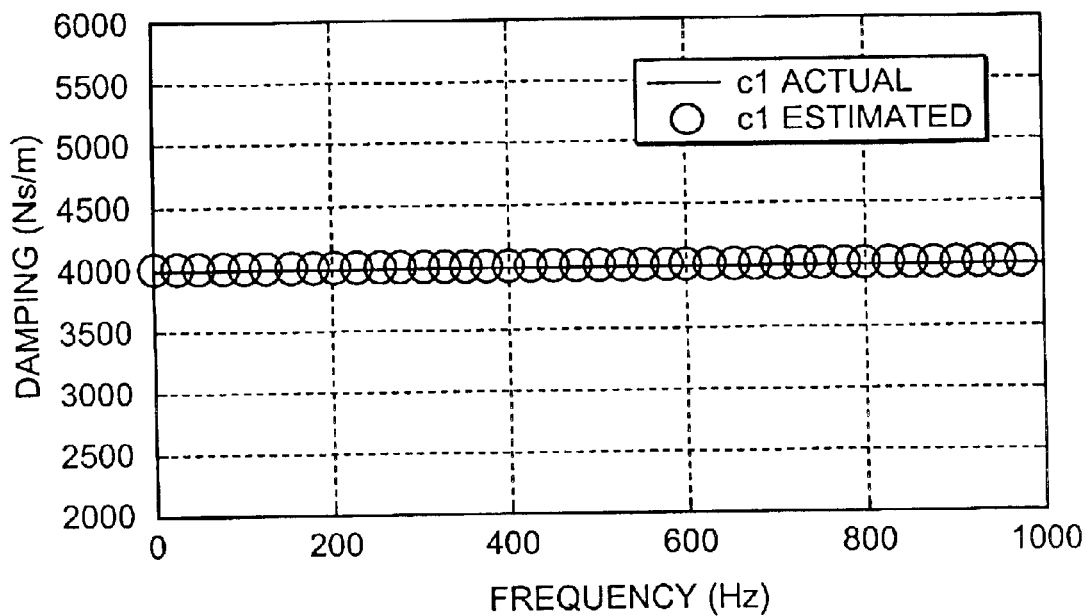
Figure 14A:
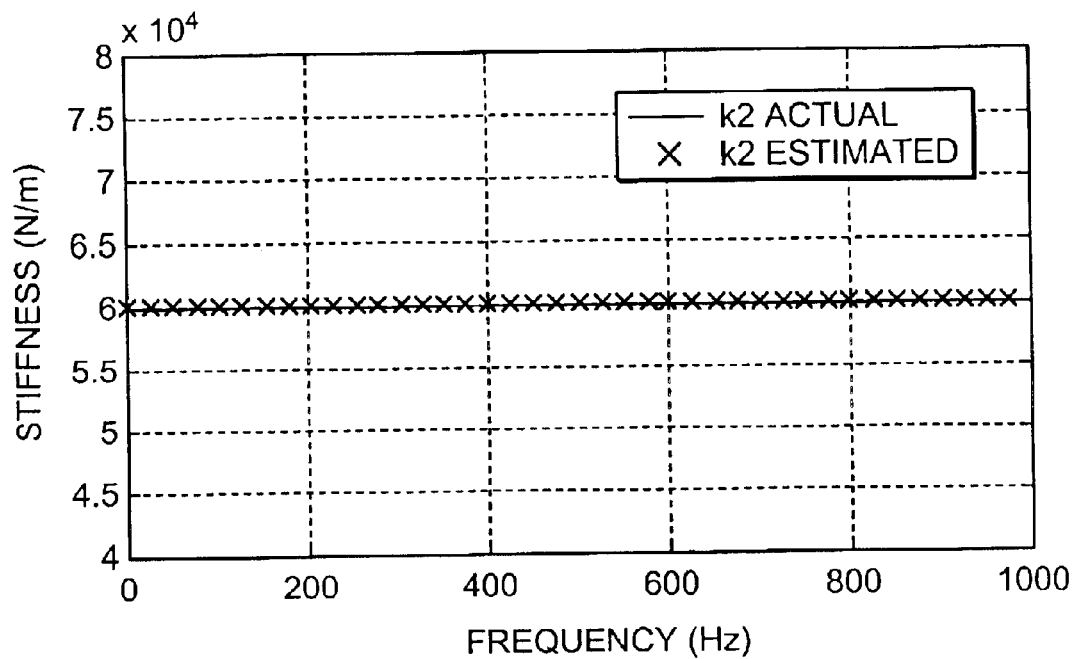
FIG. 14 is a graph of the boundary conditions of the system shown in FIG. 2 versus frequency.
Figure 14B:
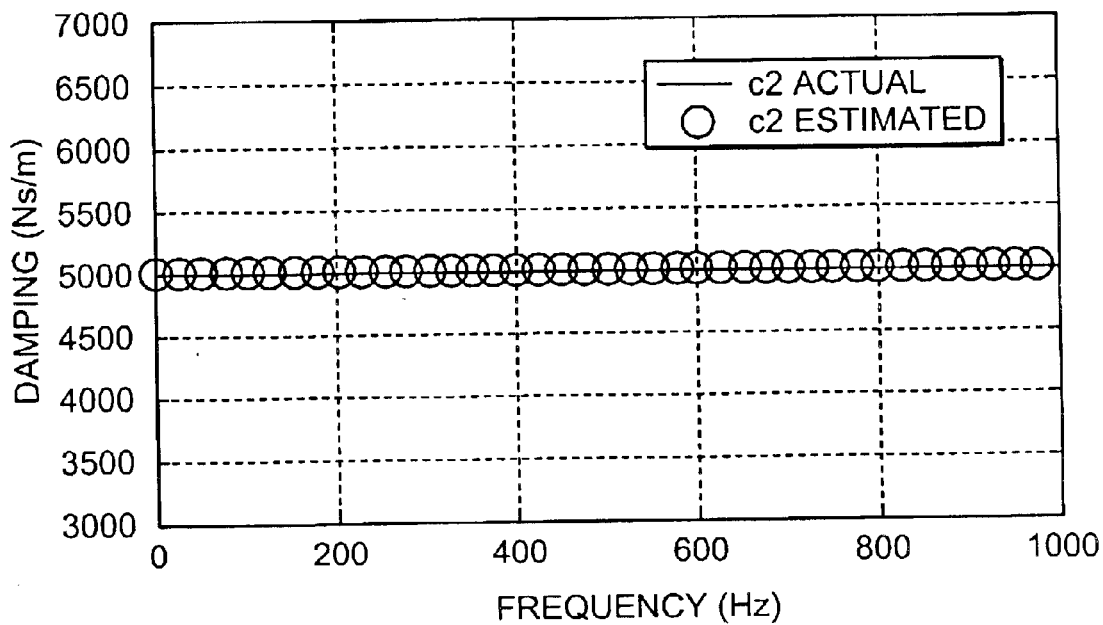

FIG. 6 graphs the function s versus frequency. It was calculated by inserting the left-hand side of equations (20)–(26) into equations (34)–(40) and represents the first step of the inverse method calculations. FIGS. 7A and 7B represent the flexural wavenumber versus frequency. The top plot, FIG. 7A, is the real part and the bottom plot, FIG. 7B, is the imaginary part. The values created using equation (4) (the forward solution) are shown as solid lines and the values calculated (or estimated) using equations (34)–(41) (the inverse solution) are shown with x's and o's. Note that there is total agreement among the forward and inverse solutions. FIGS. 8–11 are the wave propagation coefficients A, B, C, and D versus frequency, respectively. The top plots are the magnitudes and the bottom plots are the phase angles. The values created using equation (10)–(19) (the forward solution) are shown as solid lines and the values calculated using equations (43)–(46) (the inverse solution) are shown with x's and o's. FIG. 12A and FIG. 12B graph the real and imaginary parts of Young's modulus versus frequency. The actual values are shown as solid lines and the values calculated using equation (42) are shown with x's and o's. FIG. 13 is the boundary condition parameters of mount one versus frequency. The top plot is the stiffness and the bottom plot is the damping. The actual values are shown as solid lines and the values calculated using equations (47) and (48) are shown with x's and o's. FIG. 14 is the boundary condition parameters of mount two versus frequency. The top plot, FIG. 14A, is the stiffness and the bottom plot, FIG. 14B, is the damping. The actual values are shown as solid lines and the values calculated using equations (49) and (50) are shown with x's and o's.

In light of the above, it is therefore understood that within the scope of the appended claims, the invention may be practiced otherwise than as specifically described.

What is claimed is:

1. A method of determining structural properties of a flexural beam comprising the steps of:
   securing at least seven accelerometers spaced approximately equidistant from each other along a length of said beam;
   providing a transverse vibrational input to said beam at a base;
   measuring seven frequency domain transfer functions of displacement from said secured accelerometers; and
   estimating a flexural wavenumber from said seven frequency domain transfer functions;
   wherein said seven frequency domain transfer functions comprise:

$$T_{-3} = \frac{U_{-3}(-3\delta, \omega)}{V_0(\omega)} = A\cos(3\alpha\delta) - B\sin(3\alpha\delta) + C\cosh(3\alpha\delta) - D\sinh(3\alpha\delta),$$

$$T_{-2} = \frac{U_{-2}(-2\delta, \omega)}{V_0(\omega)} = A\cos(2\alpha\delta) - B\sin(2\alpha\delta) + C\cosh(2\alpha\delta) - D\sinh(2\alpha\delta),$$

$$T_{-1} = \frac{U_{-1}(-\delta, \omega)}{V_0(\omega)} = A\cos(\alpha\delta) - B\sin(\alpha\delta) + C\cosh(\alpha\delta) - D\sinh(\alpha\delta),$$

$$T_0 = \frac{U_0(0, \omega)}{V_0(\omega)} = A + C,$$

$$T_1 = \frac{U_1(\delta, \omega)}{V_0(\omega)} = A\cos(\alpha\delta) + B\sin(\alpha\delta) + C\cosh(\alpha\delta) + D\sinh(\alpha\delta),$$

$$T_2 = \frac{U_2(2\delta, \omega)}{V_0(\omega)} = A\cos(2\alpha\delta) + B\sin(2\alpha\delta) + C\cosh(2\alpha\delta) + D\sinh(2\alpha\delta), \text{ and}$$

$$T_3 = \frac{U_3(3\delta, \omega)}{V_0(\omega)} = A\cos(3\alpha\delta) + B\sin(3\alpha\delta) + C\cosh(3\alpha\delta) + D\sinh(3\alpha\delta).$$

2. The method of claim 1 further comprising the step of securing at least one accelerometer to said base.

3. The method of claim 1 further comprising securing said beam to a shaker table using a spring and a dashpot disposed at both a first and a second end of said beam.

4. The method of claim 3 further comprising the step of securing at least one accelerometer to said base.

5. The method of claim 1 wherein said base is a shaker table and further comprising:

securing a first end of said beam to the shaker table using a spring and a dashpot; and securing a second end of said beam to a fixed object by a pinned connection.

6. The method of claim 5, further comprising the step of securing at least one accelerometer to said base.

7. The method of claim 1 wherein said base is a shaker table and further comprising the steps of:

securing a first end of said beam to the shaker table using a spring and a dashpot; and securing a second end of said beam to a fixed object using a spring and a dashpot.

8. The method of claim 7 further comprising the step of securing at least one accelerometer to said base.

9. The method of claim 1 wherein said base is a shaker table and further comprising the steps of:

securing a first end of maid beam directly to the shaker table; and securing a second end of maid beam to a fixed object by a pinned connection.

10. The method of claim 9 further comprising the step of securing at least one accelerometer to said base.

11. The method of claim 1 further comprising the step of determining a complex valued modulus of elasticity at each frequency using said flexural wavenumber.

12. The method of claim 1 further comprising the step of determining wave property coefficient using said flexural wavenumber.

* * * * *